(12) United States Patent
Jung et al.

(10) Patent No.: US 11,612,333 B2
(45) Date of Patent: Mar. 28, 2023

(54) APPARATUS FOR OBTAINING BIOLOGICAL INFORMATION

(71) Applicant: SAMSUNG ELECTRONICS CO., LTD., Suwon-si (KR)

(72) Inventors: Myounghoon Jung, Bucheon-si (KR); Eunsung Park, Seongnam-si (KR); Kak Namkoong, Seoul (KR); Kunsun Eom, Seoul (KR); Yeolho Lee, Anyang-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/832,188

(22) Filed: Jun. 3, 2022

(65) Prior Publication Data
US 2022/0313106 A1  Oct. 6, 2022

Related U.S. Application Data

(63) Continuation of application No. 14/966,053, filed on Dec. 11, 2015, now Pat. No. 11,375,917.

(30) Foreign Application Priority Data

Apr. 8, 2015 (KR) .................. 10-2015-0049954

(51) Int. Cl.
*A61B 5/0537* (2021.01)
*A61B 5/00* (2006.01)
*A61B 5/026* (2006.01)

(52) U.S. Cl.
CPC ............ *A61B 5/0537* (2013.01); *A61B 5/681* (2013.01); *A61B 5/026* (2013.01); *A61B 5/6898* (2013.01)

(58) Field of Classification Search
CPC ....... A61B 5/0537; A61B 5/681; A61B 5/026; A61B 5/6898; A61B 5/4869
See application file for complete search history.

(56) References Cited

U.S. PATENT DOCUMENTS

| 4,448,199 A | 5/1984 | Schmid |
| 4,949,727 A | 8/1990 | Yamazaki et al. |

(Continued)

FOREIGN PATENT DOCUMENTS

| CN | 1319376 A | 10/2001 |
| CN | 102655806 A | 9/2012 |

(Continued)

OTHER PUBLICATIONS

Communication dated Sep. 29, 2021 issued by the Korean Intellectual Property Office in application No. 10-2015-0049954.

(Continued)

*Primary Examiner* — Rene T Towa
(74) *Attorney, Agent, or Firm* — Sughrue Mion, PLLC

(57) ABSTRACT

An apparatus for obtaining bio information includes: a first electrode portion including a current electrode and a voltage electrode arranged to contact a first body portion of a subject; a second electrode portion including a current electrode and a voltage electrode arranged to contact a second body portion of the subject; and a measuring unit configured to measure a bio impedance of the subject by applying a current to the current electrodes of the first and second electrode portions and detecting a voltage at the voltage electrodes of the first and second electrode portions. In order to decrease errors of a measured bio impedance, contact resistances of the first and second body portions of the subject contacting the current electrode and the first and second body portions of the subject contacting the voltage (Continued)

electrode are different from each other, for at least one of the first and second electrode portions.

9 Claims, 9 Drawing Sheets

(56) References Cited

U.S. PATENT DOCUMENTS

| | | | |
|---|---|---|---|
| 4,955,381 | A | 9/1990 | Way et al. |
| 5,191,891 | A | 3/1993 | Righter |
| 5,415,176 | A | 5/1995 | Sato et al. |
| 5,817,031 | A | 10/1998 | Masuo et al. |
| 6,243,651 | B1 | 6/2001 | Masuo |
| 6,473,642 | B1 * | 10/2002 | Inoue .................. A61B 5/4872 600/547 |
| 6,526,315 | B1 * | 2/2003 | Inagawa .............. A61B 5/0537 600/547 |
| 7,103,407 | B2 * | 9/2006 | Hjelt .................... A61B 5/4866 600/547 |
| 2001/0030546 | A1 | 10/2001 | Yamada et al. |
| 2002/0156378 | A1 | 10/2002 | Sakai |
| 2004/0181141 | A1 | 9/2004 | Kislov et al. |
| 2004/0215271 | A1 | 10/2004 | Sullivan |
| 2005/0054939 | A1 | 3/2005 | Ben-Ari et al. |
| 2008/0294058 | A1 | 11/2008 | Shklarski |
| 2010/0076331 | A1 | 3/2010 | Chan et al. |
| 2011/0301439 | A1 | 12/2011 | Albert et al. |
| 2014/0128691 | A1 | 5/2014 | Olivier |
| 2014/0163404 | A1 | 6/2014 | Reichman et al. |
| 2015/0025352 | A1 | 1/2015 | Caytak et al. |

FOREIGN PATENT DOCUMENTS

| | | |
|---|---|---|
| EP | 1 238 633 A1 | 9/2002 |
| GB | 2 390 429 A | 1/2004 |
| JP | 2001-157672 A | 6/2001 |
| JP | 3182991 B2 | 7/2001 |
| JP | 2002-10988 A | 1/2002 |
| JP | 2002-355230 A | 12/2002 |
| KR | 1020010106959 A | 12/2001 |
| KR | 10-1161975 B1 | 7/2012 |
| WO | 2008/032291 A2 | 3/2008 |
| WO | 2011075767 A1 | 6/2011 |

OTHER PUBLICATIONS

Communication dated May 19, 2020, from the State Intellectual Property Office of People's Republic of China in counterpart Application No. 201610203209.7.
Communication dated Sep. 2, 2016 issued by the European Patent Office in counterpart European Patent Application No. 16163108.0.

* cited by examiner

APPARATUS FOR OBTAINING BIOLOGICAL INFORMATION

CROSS-REFERENCE TO RELATED APPLICATION

This application is a continuation application of U.S. application Ser. No. 14/966,053, filed Dec. 11, 2015, which claims the benefit of Korean Patent Application No. 10-2015-0049954, filed on Apr. 8, 2015, in the Korean Intellectual Property Office, the disclosure of which are incorporated herein by reference in their entireties.

BACKGROUND

1. Field

Apparatuses and methods consistent with exemplary embodiments relate to obtaining bio information using bio impedance.

2. Description of the Related Art

With developments in medical science and extended life expectancies, interest in health care and medical devices has increased. Accordingly, various medical devices for use in hospitals and inspection clinics, medium-sized medical devices installed in government agencies, personal small-sized medical devices, and personal mobile healthcare devices have been proposed.

A body composition measurer, which is a type of health care device, measures body composition through bioelectrical impedance analysis (BIA). According to BIA, the impedance of a human body is measured by applying a current to a human body, which is considered as a combination of impedances, and measuring a voltage based on the current. Further according to BIA, the body composition such as moisture in the human body, an amount of protein, bones, and fat may be analyzed based on the measured impedance.

When body composition is measured by using a bio impedance, electrodes are directly placed in contact with a body part of a user. Thus, contact resistance generated by the contact between the contacts and the body part may affect measured bio impedance values.

SUMMARY

Provided are methods and apparatuses for obtaining bio information, which have an improved accuracy of bio impedance measurement by taking contact resistance between electrodes and body parts into account.

Additional aspects will be set forth in part in the description which follows and, in part, will be apparent from the description, or may be learned by practice of the exemplary embodiments.

According to an aspect of an exemplary embodiment, an apparatus for obtaining bio information, includes: a first electrode portion including a current electrode and a voltage electrode which are arranged to contact a first body portion of a hand of a subject; a second electrode portion including a current electrode and a voltage electrode which are arranged to contact a second body portion of the other hand of the subject; and a measuring unit configured to measure a bio impedance of the subject by applying a current to the current electrodes of the first and second electrode portions and detecting a voltage at the voltage electrodes of the first and second electrode portions. Contact resistances of the first and second body portions of the subject contacting the current electrode and the first and second body portions of the subject contacting the voltage electrode are different from each other, for at least one of the first and second electrode portions.

For at least one of the first and second electrode portions, the current electrode may have an area greater than an area of the voltage electrode.

For the at least one of the first and second electrode portions, the current electrode and the voltage electrode may be shaped corresponding to portions of a divided polygon, a divided circle, or a divided oval.

For the at least one of the first and second electrode portions, the current electrode and the voltage electrode may be arranged such that the first electrode portion or the second electrode portion is polygonal shaped, circular shaped, or oval shaped.

For the at least one of the first and second electrode portions, one of the current electrode and the voltage electrode surrounds at least a portion of the other of the current electrode and the voltage electrode.

For the at least one of the first and second electrode portions, the current electrode may be circular, oval, or polygonal shaped.

For the at least one of the first and second electrode portions, the voltage electrode may be circular ring shaped, oval ring shaped, or polygonal ring shaped and surrounds the current electrode.

For the at least one of the first and second electrode portions, the current electrode and the voltage electrode may be respectively circular shaped and circular ring shaped and satisfy a following condition:

$$a > \frac{-d + \sqrt{2b^2 - d^2}}{2}$$

where, a is a radius of the current electrode, b is an external radius of the voltage electrode, and d is a distance between the current electrode and the voltage electrode.

For the at least one of the first and second electrode portions, the current electrode and the voltage electrode may be respectively square shaped and square ring shaped and satisfy a following condition:

$$a > \frac{-d + \sqrt{2b^2 - d^2}}{2}$$

where, a is a length of a side of the current electrode, b is a length of an external side of the voltage electrode, and d is a distance between the current electrode and the voltage electrode.

For the at least one of the first and second electrode portions, the current electrode and the voltage electrode may be respectively oval shaped and oval ring shaped and have length ratios that are equal to k. The length ratio of the current electrode may be the ratio of a long axis of the current electrode to a short axis of the current electrode, and the length ratio of the voltage electrode may be the ratio of a long axis of the voltage electrode to a short axis of the voltage electrode. The current electrode and the voltage electrode satisfy a following condition:

$$a > \frac{-(k+1)d + \sqrt{(k+1)^2 d^2 - 8k(d^2 - kb^2)}}{4k}$$

where, a is a length of a short axis of the current electrode, b is a length of a short axis of an external oval of the voltage electrode, and d is a distance between the current electrode and the voltage electrode.

For the at least one of the first and second electrode portions, the voltage electrode may be circular shaped, oval shaped, or polygonal shaped, and the current electrode may be circular ring shaped, oval ring shaped, or polygonal ring shaped and may surround the voltage electrode.

The apparatus may further include an analysis unit configured to analyze bio information of the subject based on the bio impedance measured by the measuring unit.

The bio information may include body composition or blood volume.

The apparatus may be a wrist-wearable apparatus including a main body and strap.

The first electrode portion may be arranged on an inner surface of the main body or an inner surface of the strap and may come into contact with a wrist of the subject. The second electrode portion may be arranged on an outer surface of the main body or an outer surface of the strap.

The apparatus may be a portable device including a front surface on which a display unit is arranged, a rear surface opposite to the front surface, and side portions connecting the front and rear surfaces.

One of the first and second electrode portions may be arranged on the side portions, and the other of the first and second electrode portions may be arranged on the front surface.

One of the first and second electrode portions may be arranged on the side portions, and the other of the first and second electrode portions may be arranged on the rear surface.

One of the first and second electrode portions may be arranged on the front surface, and the other of the first and second electrode portions may be arranged on the rear surface.

According to an aspect of another exemplary embodiment, an apparatus for obtaining bio information is provided. The apparatus includes: a first electrode portion comprising a first current electrode and a first voltage electrode; a second electrode portion comprising a second current electrode and a second voltage electrode; and a measuring unit configured to measure a bio impedance by applying a current to the current electrodes of the first and second electrode portions and detecting a voltage at the voltage electrodes of the first and second electrode portions. The contact resistances between the first current electrode and the first voltage electrode may be different from each other or the contact resistances between the second current electrode and the second voltage electrode may be different from each other.

The first current electrode may have an area greater than an area of the first voltage electrode.

The first current electrode and the first voltage electrode may comprise a shape corresponding to a divided polygon, a divided circle, or a divided oval.

The apparatus may include an analysis unit configured to analyze bio information based on the bio impedance measured by the measuring unit.

The bio information may include body composition or blood volume.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
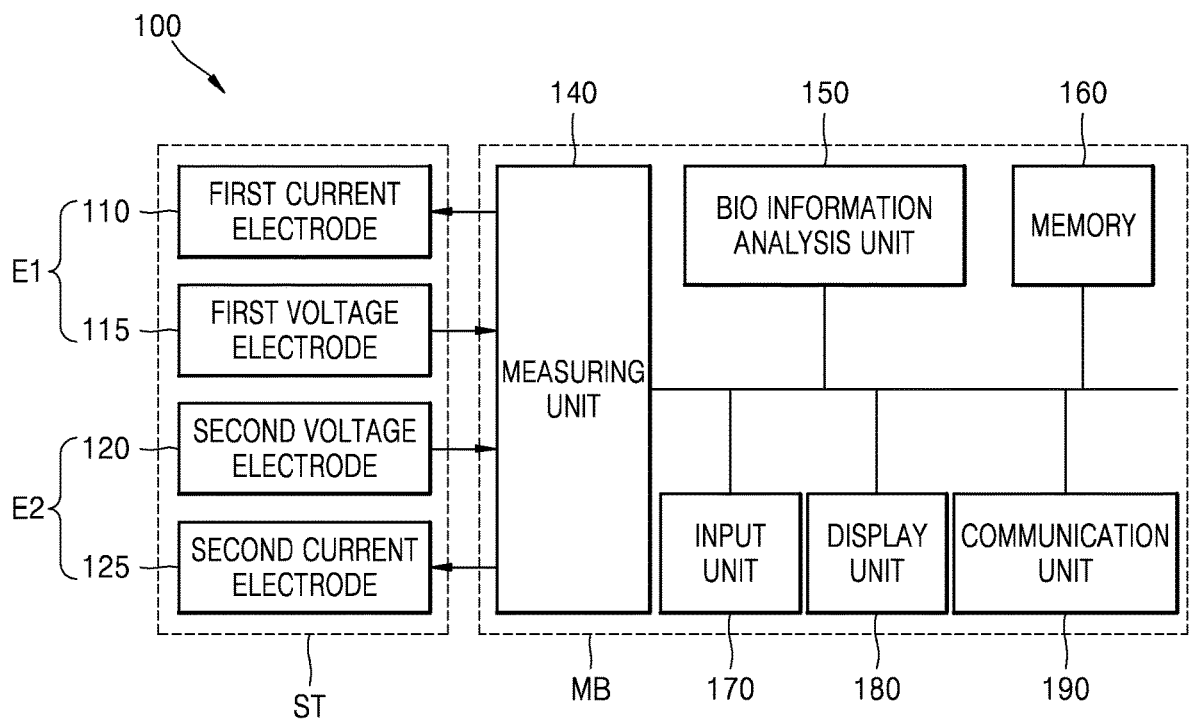
FIG. 1 illustrates a block diagram of a schematic structure of an apparatus for obtaining bio information according to an exemplary embodiment.

The inventive concept will now be described more fully with reference to the accompanying drawings, in which exemplary embodiments are shown.

Like reference numerals in the drawings denote like elements.

It will be understood that when a component, such as a layer, a film, a region, or a plate, is referred to as being "on" another component, the component can be directly on the other component or intervening components may be present thereon.

While such terms as "first", "second", etc., may be used to describe various components, such components must not be limited to the above terms. The above terms are used only to distinguish one component from another.

An expression used in the singular encompasses the expression of the plural, unless it has a clearly different meaning in the context. In the present specification, it is to be understood that terms such as "including", "having", and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

In the present specification, it will be understood that a term such as a "unit" is intended to indicate a hardware component such as a processor or a circuit, and/or a software component implemented by a hardware component such as a processor.

Figure 2A:
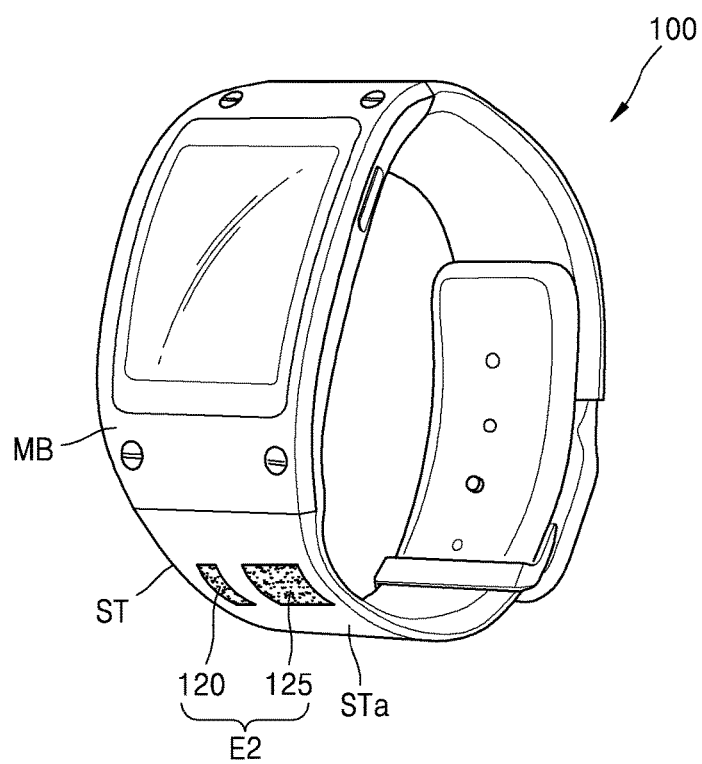
FIGS. 2A and 2B illustrate perspective views of an exterior of an apparatus for obtaining bio information and respectively illustrate arrangements of a first electrode portion and a second electrode portion.
Figure 2B:
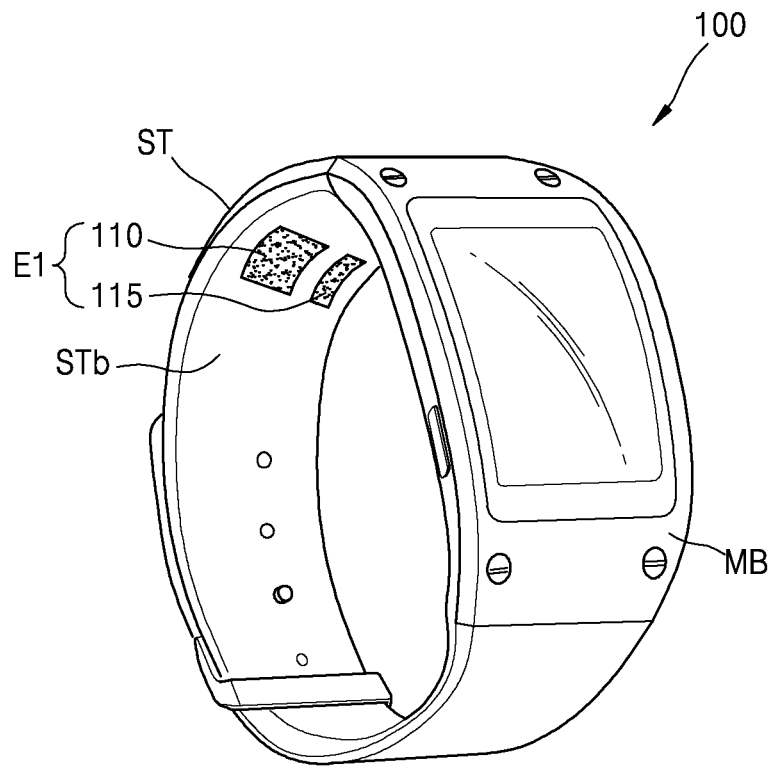
Figure 3:
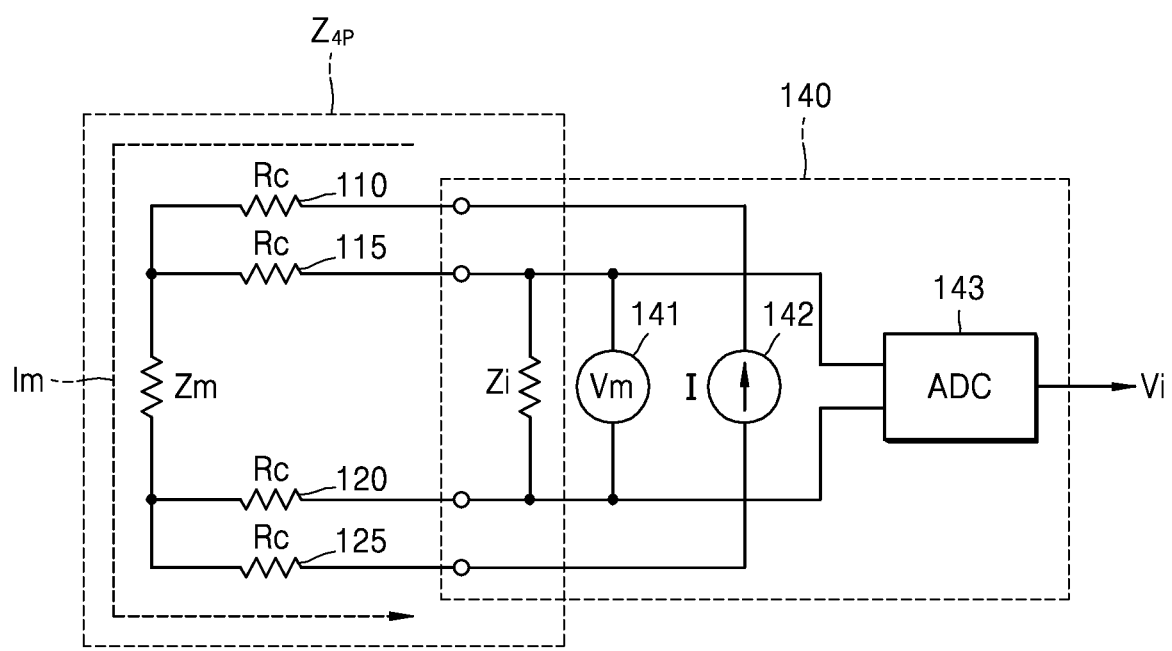
FIG. 3 illustrates a circuit diagram for electrode portions and a measuring unit in the apparatus for obtaining bio information of FIG. 1.

FIG. 1 illustrates a block diagram of a schematic structure of an apparatus 100 for obtaining bio information according to an exemplary embodiment, FIGS. 2A and 2B illustrate perspective views of an exterior of the apparatus 100 for obtaining bio information and respectively illustrate arrangements of a first electrode portion E1 and a second electrode portion E2, and FIG. 3 illustrates a circuit diagram for first and second electrode portions E1 and E2 and a measuring unit 140 in the apparatus 100 for obtaining bio information of FIG. 1.

The apparatus 100 for obtaining bio information may include: the first electrode portion E1 including a pair of a current electrode 110 and a voltage electrode 115 which are arranged to come into contact with a part of one hand of a subject; the second electrode portion E2 including a pair of a current electrode 125 and a voltage electrode 120 which are arranged to come into contact with a part of the other hand of the subject; and the measuring unit 140 for measuring a bio impedance of the subject by applying a current to the current electrodes 110 and 125 and detecting a voltage across the voltage electrodes 115 and 120.

In the present exemplary embodiment, at least one of the first electrode portion E1 and the second electrode portion E2 may have different contact resistance when body parts of the subject respectively come into contact with the current electrodes 110 and 125 and the voltage electrodes 115 and 120. For example, for at least one of the first electrode portion E1 and the second electrode portion E2, an area of the current electrode 110 may be different from an area of the voltage electrode 115 or an area of the current electrode 125 may be different from an area of the voltage electrode 120.

The apparatus 100 for obtaining bio information may further include a bio information analysis unit 150 for analyzing bio information of the subject based on the bio impedance measured by the measuring unit 140. The bio information may be, for example, body composition such as body fat, moisture content, muscle strength, an edema value, or blood volume.

The apparatus 100 for obtaining bio information may further include, for example, a memory 160, an input unit 170 (e.g., an input device, touch screen, touch panel, button, etc.), a display unit 180 (e.g., a display, etc.), and a communication unit 190 (e.g., a transceiver, etc.).

The apparatus 100 for obtaining bio information may be a wearable apparatus, for example, a wrist-wearable apparatus including a main body MB and straps ST. In the drawings, the first and second electrode portions E1 and E2 are placed on the straps ST, and the measuring unit 140, the bio information analysis unit 150, the memory 160, the input unit 170, the display unit 180, and the communication unit 190 are placed on the main body MB. However, the inventive concept is not limited thereto.

As illustrated in FIGS. 2A and 2B, the apparatus 100 for obtaining bio information includes the main body MB and the straps ST. The straps ST are connected to the main body MB and may be wearable on a wrist of the subject. The first current electrode 110 and the first voltage electrode 115 are arranged on an inner surface STb of any one of the straps ST, and the second current electrode 120 and the second voltage electrode 125 are arranged on an outer surface STa of any one of the straps ST.

The first current electrode 110 and the first voltage electrode 115 are electrodes contacting a wrist of the subject when a user, that is, the subject whose body composition is to be measured, wears the apparatus 100 for obtaining bio information. The first current electrode 110 and the first voltage electrode 115 may be arranged on locations where the first current electrode 110 and the first voltage electrode 115 may contact the wrist of the subject, but the locations are not limited to the inner surface STb of the straps ST. For example, the first current electrode 110 and the first voltage electrode 115 may be arranged on an inner surface of the main body MB.

The second current electrode 120 and the second voltage electrode 125 are electrodes contacting a part of the other wrist on which the apparatus 100 for obtaining bio information is not placed. The second current electrode 120 and the second voltage electrode 125 may be arranged to be exposed to the outside of the apparatus 100 for obtaining bio information such that the second current electrode 120 and the second voltage electrode 125 may contact a part of the other wrist. However, locations of the second current electrode 120 and the second voltage electrode 125 are not limited to the outer surface STa of the straps ST. For example, the second current electrode 120 and the second voltage electrode 125 may be arranged on an outer surface of the main body MB.

The first current electrode 110 and the first voltage electrode 115 respectively face the second current electrode 120 and the second voltage electrode 125, but the first current electrode 110 and the first voltage electrode 115 may not accurately face the second current electrode 120 and the second voltage electrode 125. The first current electrode 110, the first voltage electrode 115, the second current electrode 120, and the second voltage electrode 125 are arranged in a direction perpendicular to a lengthwise direction of the straps ST, but the inventive concept is not limited thereto. The first current electrode 110, the first voltage electrode 115, the second current electrode 120, and the second voltage electrode 125 may be arranged in another direction, for example, a direction parallel to the lengthwise direction of the straps ST, or other directions. In the first electrode portion E1 and the second electrode portion E2, areas of the current electrodes 110 and 125 are greater than areas of the voltage electrodes 115 and 120, but the present exemplary embodiment is not limited thereto. In any one of the first electrode portion E1 and the second electrode portion E2, for example, only in the second electrode portion E2, an area of the current electrode 125 may be greater than an area of the voltage electrode 120. Shapes of the current electrodes 110 and 125 and the voltage electrodes 115 and 120 are not limited thereto.

Referring back to FIG. 1, other components of the apparatus 100 for obtaining bio information will be described.

The bio information analysis unit 150 may analyze bio information of the subject by using the bio impedance measured by the measuring unit 140. For example, body composition such as characteristics of skin (for example, moisture content), muscle strength, and an edema value, or blood volume may be analyzed based on the bio impedance. The bio impedance, the user, that is, the body information of the subject may be used to analyze the bio information. The bio information may be an age, height, weight, etc. of the user and may be received from the current unit 170.

Various operations used by the bio information analysis unit 150 may be stored as programs in the memory 160 and executed by a processor (not shown). The processor may be hardware for controlling overall functions and operations of the apparatus 100 for obtaining bio information, and the bio information may be analyzed by the bio information analysis unit 150 when the programs stored in the memory 160 are executed. In addition, the processor may control the measuring unit 140 to measure a bio impedance and may process an analysis result as an image signal for displaying an analysis result on the display unit 180.

The memory 160 may store programs for operations of the apparatus 100 for obtaining bio information, data used for the programs, etc. therein. The memory 160 is a conventional storage medium and may include, for example, a hard disk drive (HDD), read only memory (ROM), random access memory (RAM), flash memory, and a memory card.

The memory 160 may store programs for operations to be performed by the bio information analysis unit 150 therein. Additional data such as an age, weight, gender, etc. of the subject may be stored in the memory 160.

The input unit 170 and the display unit 180 form an interface between the apparatus 100 for obtaining bio information and the subject or a user.

An input for manipulating the apparatus 100 for obtaining bio information may be received via the input unit 170, and a result output from the bio information analysis unit 150 may be displayed on the display unit 180.

The input unit 170 may include a button, a keypad, a switch, a dial, or a touch interface used by the subject to directly manipulate the apparatus 100 for obtaining bio information.

The display unit 180 that is a display panel for outputting an analysis result may include a liquid crystal display (LCD) panel, an organic light-emitting display (OLED) panel, or the like, and may display information about an analysis result of the body composition as an image or text. The display unit 180 may be a touch screen capable of receiving an input or displaying an output.

Moreover, the display unit 180 may include an input/output (I/O) port for connecting human interface devices (HIDs) to one another and an I/O port for inputting/outputting an image.

The communication unit 190 may transmit the analysis result to an external device in a wired or wireless manner. The external device may be, for example, a medical apparatus using analyzed bio information, a printer for printing an analysis result, or a display apparatus for displaying an analysis result. Alternatively, the external device may be a smart phone, a mobile phone, a personal digital assistant (PDA), a laptop computer, a PC, another mobile device or a non-mobile computing device, but is not limited thereto.

The communication unit 190 may be connected to the eternal device in a wired or wireless manner. For example, the communication unit 190 may communicate with the eternal device by a Bluetooth communication method, a Bluetooth low energy (BLE) communication method, a near field communication (NFC) communication method, a wireless LAN (WLAN) communication method, a Zigbee communication method, an infrared data association (IrDA) communication method, a Wi-Fi direct (WFD) communication method, a ultra wideband (UWB) communication method, an Ant+ communication method, and a Wi-Fi communication method, but the communication method is not limited thereto.

As illustrated in FIGS. 2A and 2B, in the apparatus 100 for obtaining bio information that is a small electronic device, small electrodes are used to measure a bio impedance. However, as sizes of the electrodes decrease, contact resistance generated by contact of the electrodes with a body part may increase. The contact resistance affects the measurement of the bio impedance. A large electrode area may be advantageous for decreasing the contact resistance, but when the apparatus 100 for obtaining bio information is a wearable device, there is a limit on increasing the electrode area.

In the apparatus 100 for obtaining bio information, in order to accurately measure the bio impedance, sizes of the current electrodes 110 and 125 may be different from those of the voltage electrodes 115 and 120 by considering the contact resistance, and detailed descriptions thereof are as follows.

A circuit configuration via which the measuring unit 140 measures the bio impedance will be briefly described with reference to FIG. 3.

The measuring unit 140 measures the bio impedance by a bio impedance analyzer (BIA) method. As illustrated, the bio impedance of the subject may be measured by a 4-point measuring method. That is, the measuring unit 140 may measure an impedance by applying a constant current Im via two of four electrodes, measuring a voltage via the other two of four electrodes, and calculating a ratio of the voltage to the applied constant current.

Zm indicates a bio impedance, and Rc indicates contact resistance, that is, resistance generated due to contact of the current and voltage electrodes 110, 115, 120 and 125 with a body part of the subject. Zi indicates an impedance of analog front end (AFE).

The measuring unit 140 includes a voltmeter 141, a current source 142, and an analog to digital converter (ADC) 143.

The current source 142 applies a current to a human body via the current electrodes 110 and 125. The current source 142 may apply a constant current to the human body.

The voltmeter 141 measures a voltage via the voltage electrodes 115 and 120. The voltmeter 141 outputs the measured voltage to the ADC 143.

The ADC 143 converts a voltage that is input as an analog signal to a digital signal. Since magnitude of the current is fixed, magnitude of the measured voltage is proportional to a size of the bio impedance Zm. A voltage Vi measured by the measuring unit is proportional to an impedance $Z_{4P}$, and the impedance $Z_{4P}$ may be equal to the voltage Vi divided by current. The impedance $Z_{4P}$ may be described as follows.

$$Z_{4P} = f_1(Z_m, R_c, Z_i) = Z_m \frac{1}{1 + \frac{Z_m + 2R_c}{Z_i}} \qquad \text{[Equation 1]}$$

Referring to the Equation 1, $Z_{4P}$ is determined by Zm, Rc, and Zi. Zi is the impedance of the AFE and is determined according to characteristics of the AFE. $Z_{4P}$ is an impedance measured by the voltmeter 141. Zm is a bio impedance to be measured, and Rc is the contact resistance.

Referring to the Equation 1, if Zi is infinite, $Z_{4P}$ is equal to Zm. However, Zi is actually finite, $Z_{4P}$ is smaller than Zm as the contact resistance increases. In other words, as the contact resistance increases, the measured bio impedance may be smaller than an actual bio impedance.

When contact resistance of a current electrode increases, a time taken to stabilize a measurement value, and thus the measurement value may have an error.

As described above, when the bio impedance is measured, a constant current of a sine wave is applied to the current electrodes 110 and 125, and a voltage signal generated based on the bio impedance is measured by the voltage electrodes 115 and 120 and may thereby be used to calculate the bio impedance Zm. In this case, resistance driven by a constant current is an impedance element which includes the contact resistance Rc and the bio impedance Zm, and voltages applied to both ends of the current source 142 are as follows.

$$V = I_m \times (2R_C + Z_m) \quad \text{[Equation 2]}$$

Referring to Equation 2, when the contact resistance Rc increases, voltages applied to the both ends of the current source 142 having a constant current increase and then may exceed a dynamic range. Thus, an output current value may have an error, and an output wave form may be distorted. Voltage signals may not be stabilized, since the current source 142 abnormally operates.

Figure 4:
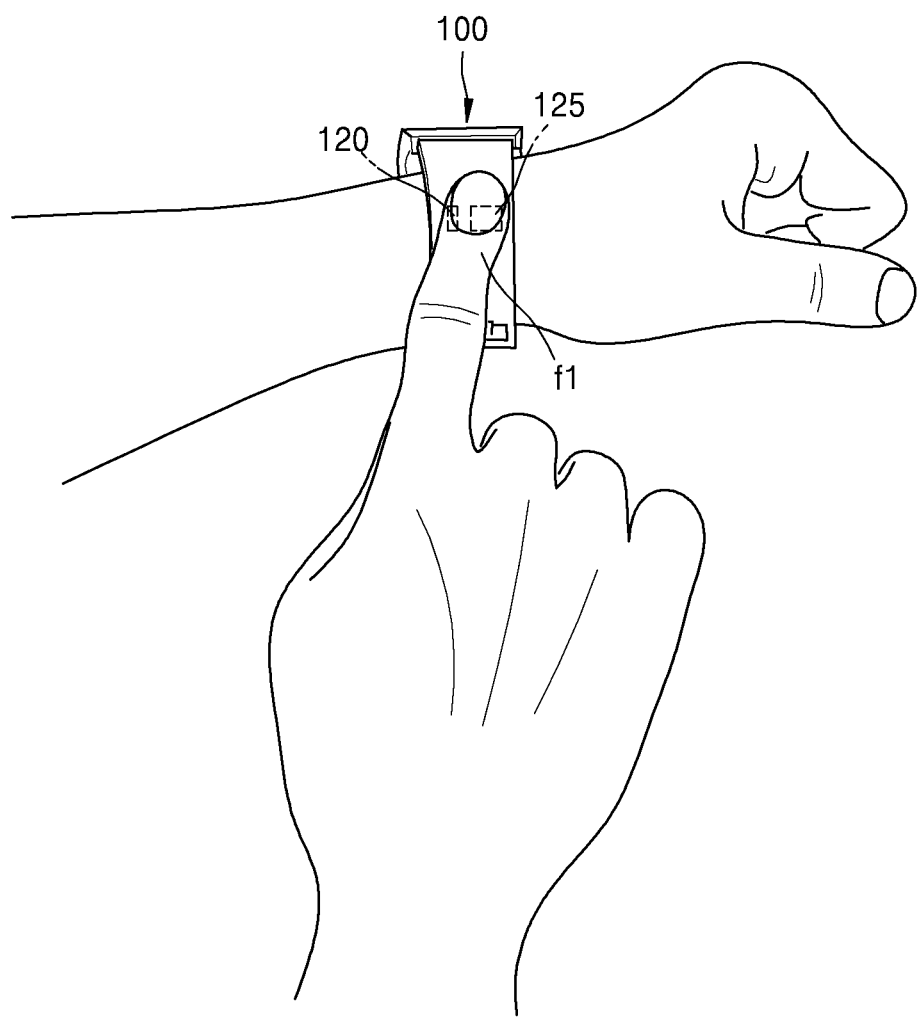
FIG. 4 illustrates a case where a body part of a subject comes into contact with an electrode portion when a bio impedance is measured using an apparatus for obtaining bio information according to an exemplary embodiment.
Figure 5:
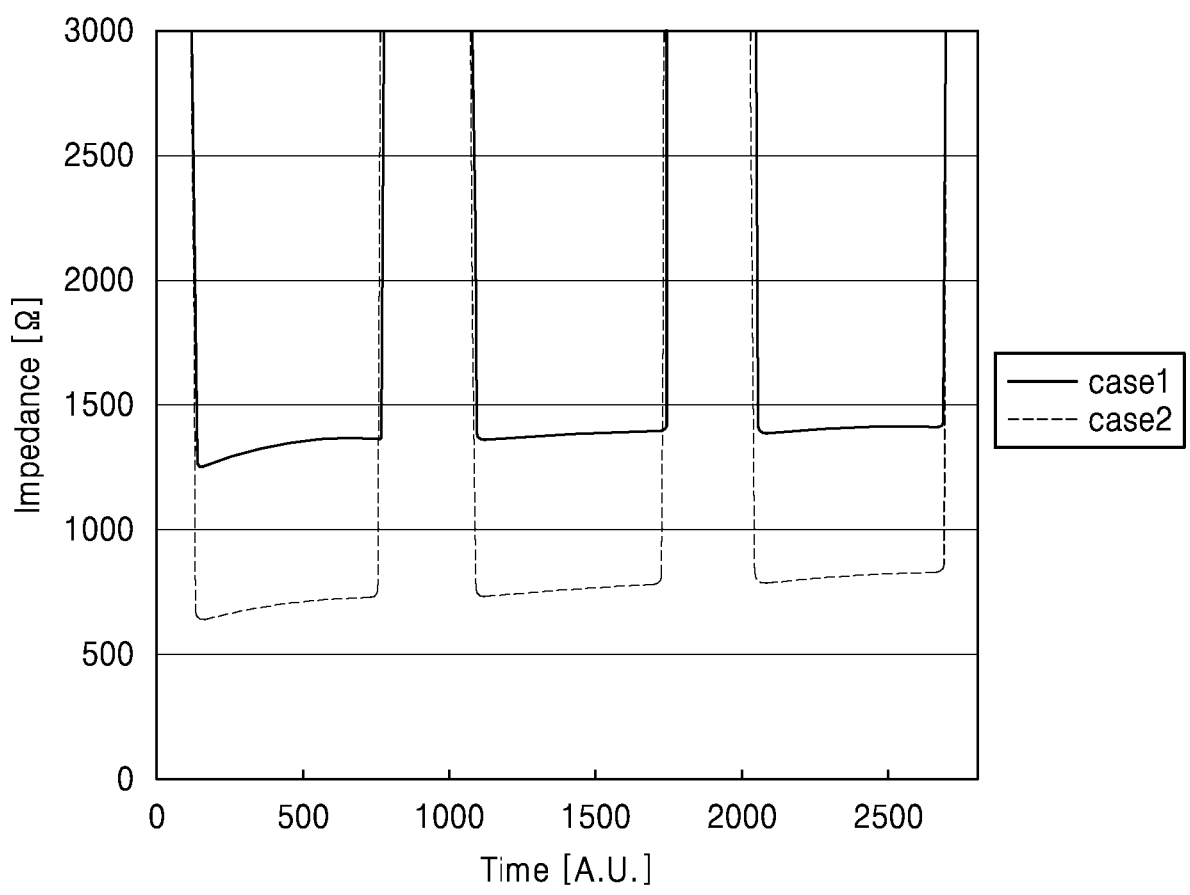
FIGS. 5 and 6 illustrate a change of a measured bio impedance according to contact resistance between a subject and electrodes.
Figure 6:
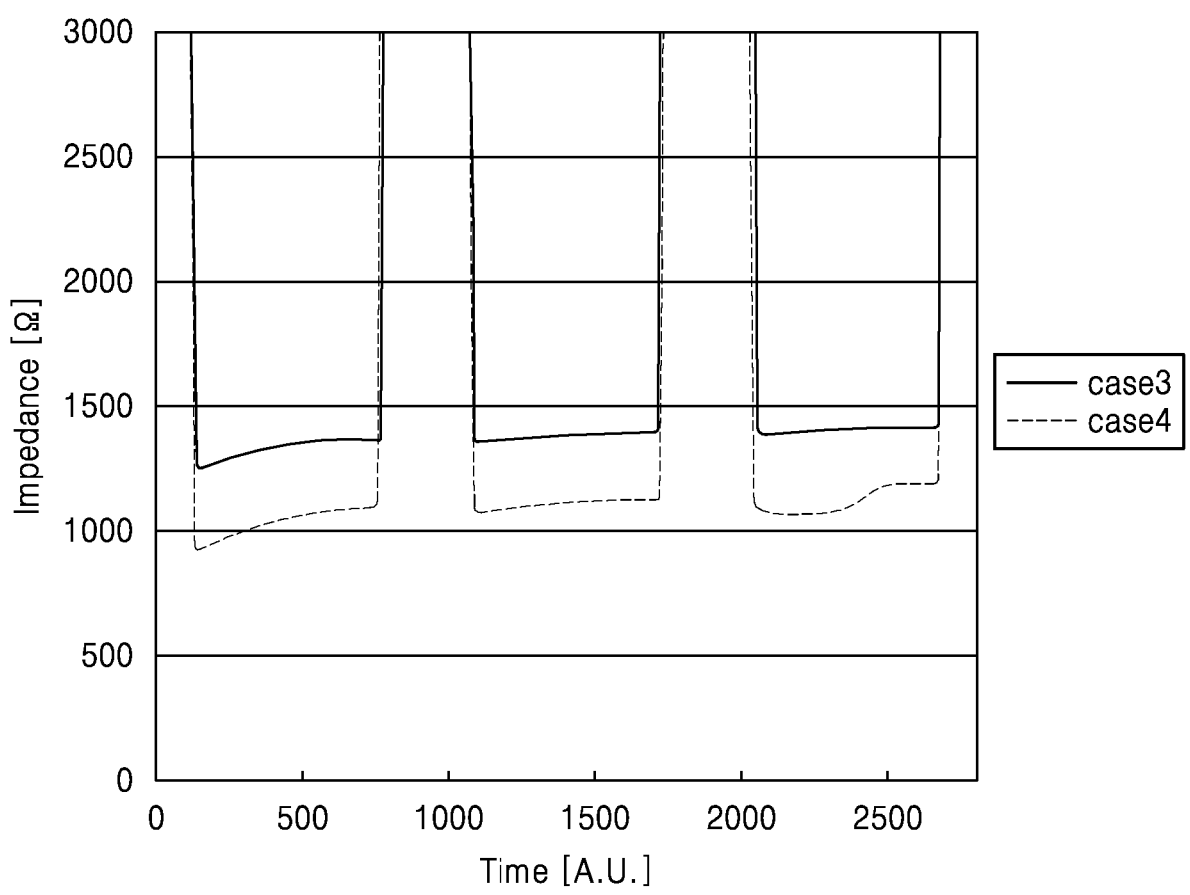

FIG. 4 illustrates a case where a body part of a subject comes into contact with an electrode portion when a bio impedance is measured using the apparatus 100 for obtaining bio information according to an exemplary embodiment, and FIGS. 5 and 6 illustrate a change of the measured bio impedance according to contact resistance between a subject and electrodes.

Referring to FIG. 4, the subject wears the apparatus 100 for obtaining bio information on a wrist and may touch the current electrode 125 and the voltage electrode 120 with fingers of the other hand. In this case, it is advantageous to fully touch the current electrode 125 and the voltage electrode 120 with the finger f1 in order to decrease the contact resistance. However, it may be uncomfortable to fully touch the current electrode 125 and the voltage electrode 120 according to shapes, areas, arrangements, etc. thereof. Therefore, the current electrode 125 and the voltage electrode 120 may be shaped such that the current electrode 125 and the voltage electrode 120 may easily contact the subject, which greatly affects a measurement result. For example, an area of the current electrode 125 may be greater than an area of the voltage electrode 120.

A result of testing the above design is as follows.

FIG. 5 is a graph showing a result of measuring an impedance while contact resistance of a current electrode changes. A case 1 is a state in which a finger is fully placed in contact with the current electrode, and a case 2 is a state in which half of a finger is placed in contact with the current electrode. That is, in the case 2, contact resistance of the current electrode is two times as great as contact resistance in the case 1. A measurement value of an impedance in the case 1 is smaller than a measurement value of an impedance in the case 2.

FIG. 6 is a graph showing a result of measuring an impedance while contact resistance of a voltage electrode changes. A case 3 is a state in which a finger is fully placed in contact with the voltage electrode, and a case 4 is a state in which half of a finger is placed in contact with the voltage electrode. That is, in the case 4, contact resistance of the voltage electrode is two times as great as contact resistance in the case 3. A measurement value of an impedance in the case 3 is smaller than a measurement value of an impedance in the case 4.

Referring to the above graphs, errors of the measured impedance according to an increase of the contact resistance may be sensitive to the contact resistance of the current electrode rather than the contact resistance of the voltage electrode.

According to analysis results, electrodes are designed in such a way that the contact resistance of the current electrode is smaller than the contact resistance of the voltage electrode.

Hereinafter, exemplary shapes of a current electrode and a voltage electrode will be described.

FIGS. 7A to 7F illustrate examples of shapes of a current electrode ELC and a voltage electrode ELV.

As illustrated in FIGS. 7A to 7F, in the first electrode portion E1 or the second electrode portion E2, an area of a current electrode ELC is set to be greater than an area of a voltage electrode ELV. The areas of the current electrode ELC and the voltage electrode ELV may be determined as follows. A sum of the areas of the current electrode ELC and the voltage electrode ELV is set to be the greatest under predetermined conditions. In this case, areas or locations where the current electrode ELC and the voltage electrode ELV are arranged, or body parts to be placed in contact with the current electrode ELC and the voltage electrode ELV are considered. For example, when a finger contacts the current electrode ELC and the voltage electrode ELV, if the areas of the current electrode ELC and the voltage electrode ELV are excessively greater than areas where the fingers may contact, a decrease of the contact resistance may be slight. After an entire area is determined, areas of the electrodes, that is, the areas of the current electrode ELC and the voltage electrode ELV, are assigned, and in this case, the area of the current electrode ELC is greater than that of the voltage electrode ELV. Thus, a distribution of the contact resistance may be optimized to decrease errors in measuring the bio impedance.

As illustrated in FIGS. 7A to 7F, the current electrode ELC and the voltage electrode ELV may have shapes corresponding to portions of a divided polygon, a divided circle, or a divided oval. For example, shapes and locations of the current electrode ELC and the voltage electrode ELV may be determined such that exteriors of the first electrode portion E1 and the second electrode portion E2 may be polygonal shaped, circular shaped, or oval shaped.

As described above, the areas of the current electrode ELC and the voltage electrode ELV may be determined by taking the entire area and the distribution of contact resistance into account. Additionally, convenient contact with body parts may also be considered.

Figure 7A:
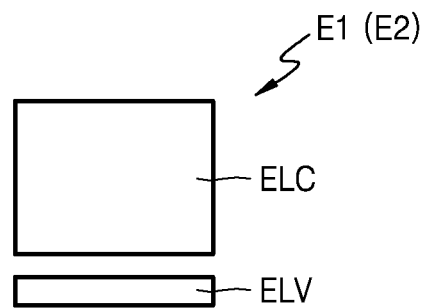
FIGS. 7A to 7F illustrate examples of shapes of a current electrode and a voltage electrode.
Figure 7B:
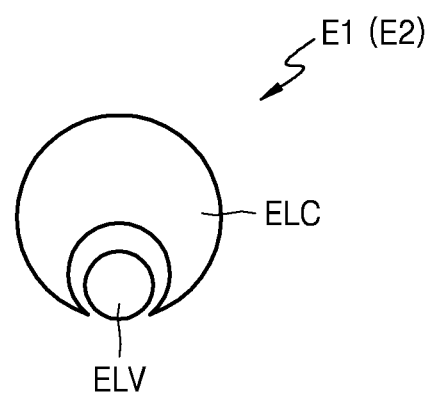
Figure 7C:
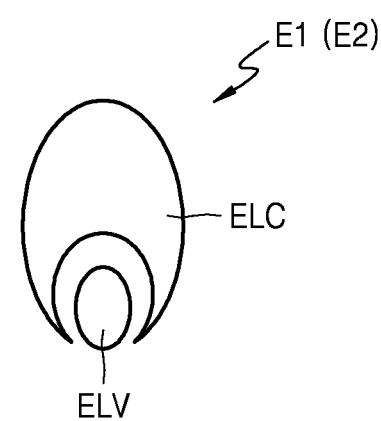
Figure 7D:
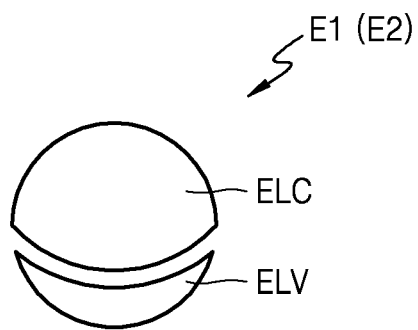
Figure 7E:
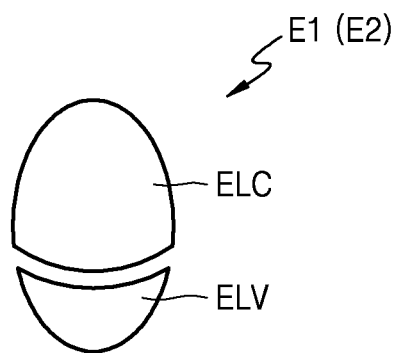
Figure 7F:
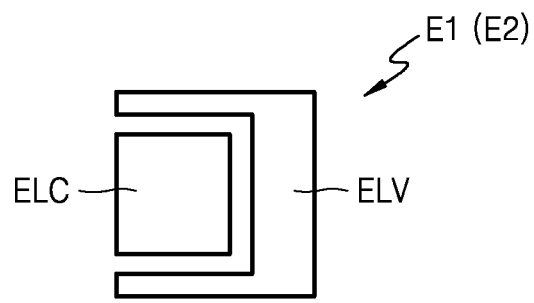

As illustrated in FIGS. 7B, 7C, and 7F, the current electrode ELC and the voltage electrode ELV may have a shape in which any one of the current electrode ELC and the voltage electrode ELV surrounds at least a portion of the other one of the current electrode ELC and the voltage electrode ELV.

Figure 8A:
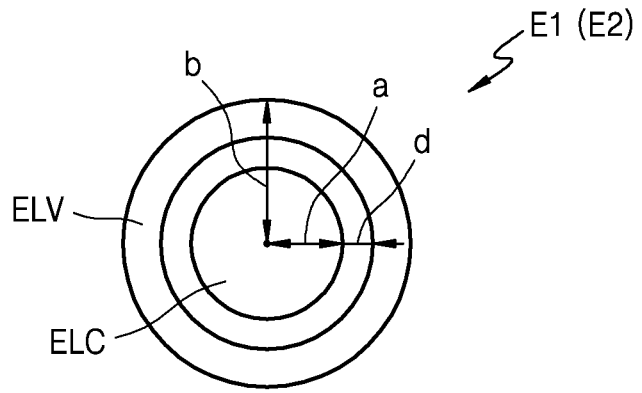
FIGS. 8A to 8C illustrate other examples of shapes of a current electrode and a voltage electrode.
Figure 8B:
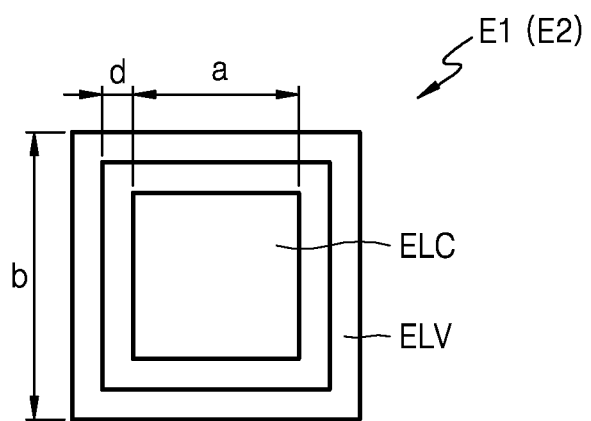
Figure 8C:
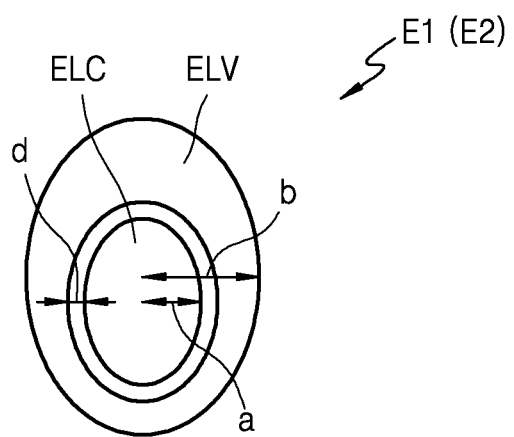

FIGS. 8A to 8C illustrate other examples of shapes of the current electrode ELC and the voltage electrode ELV.

A shape of the first electrode portion E1 or the second electrode portion E2 is determined in such a way that, for example, the subject may easily touch the electrodes with fingers by taking a position of the subject into account.

The current electrode ELC and the voltage electrode ELV may have a shape in which any one of the current electrode ELC and the voltage electrode ELV surrounds at least a portion of the other one of the current electrode ELC and the voltage electrode ELV. As illustrated in FIGS. 8A to 8C, the voltage electrode ELV may be arranged to surround an entire portion of the current electrode ELC.

The current electrode ELC may be circular shaped, oval shaped, or polygonal shaped. The voltage electrode ELV may be circular ring shaped, oval ring shaped, or polygonal ring shaped and surrounds the current electrode ELC. FIG. 8B illustrates a square ring shape, but the shape of the current electrode ELC and the voltage electrode ELV is not limited thereto.

As illustrated in FIG. 8A, the current electrode ELC and the voltage electrode ELV may respectively be circular shaped and circular ring shaped, and in this case, the following condition may be satisfied such that an area of the current electrode ELC may be greater than an area of the voltage electrode ELV.

$$a > \frac{-d + \sqrt{2b^2 - d^2}}{2} \quad \text{[Equation 3]}$$

where, a is a radius of the current electrode ELC, b is an external radius of the voltage electrode ELV, and d is a distance between the current electrode ELC and the voltage electrode ELV.

As illustrated in FIG. 8B, the current electrode ELC and the voltage electrode ELV may respectively have square and square ring shapes, and in this case, the following condition may be satisfied such that the area of the current electrode ELC may be greater than the area of the voltage electrode ELV.

$$a > \frac{-d + \sqrt{2b^2 - d^2}}{2} \quad \text{[Equation 4]}$$

where, a is a length of a side of the current electrode ELC, b is a length of an external side of the voltage electrode ELV, and d is a distance between the current electrode ELC and the voltage electrode ELV.

As illustrated in FIG. 8C, the current electrode ELC and the voltage electrode ELV may respectively be oval or oval ring shaped. The oval shapes of the current electrode ELC and the voltage electrode ELV are similar, as respective length ratios of the current electrode ELC and the voltage electrode ELV are both equal to k. The length ratio of the current electrode ELC is the ratio of a long axis of the current electrode ELC to a short axis of the current electrode ELC, and the length ratio of the voltage electrode ELV is the ratio of a long axis of the voltage electrode ELV to a short axis of the voltage electrode ELV. The following condition may be satisfied such that the area of the current electrode ELC may be greater than the area of the voltage electrode ELV.

$$a > \frac{-(k+1)d + \sqrt{(k+1)^2 d^2 - 8k(d^2 - kb^2)}}{4k} \quad \text{[Equation 5]}$$

where, a is a length of a short axis of the current electrode ELC, b is a length of a short axis of an external oval of the voltage electrode ELV, and d is a distance between the current electrode ELC and the voltage electrode ELV.

FIGS. 8A to 8C illustrate that the voltage electrode ELV surrounds the current electrode ELC, but this is merely an example. The current electrode ELC may surround the voltage electrode ELV. In this case, direction of inequality signs of Equations 3 to 5 may be reversed such that the area of the current electrode ELC may be greater than the area of the voltage electrode ELV.

Figure 9:
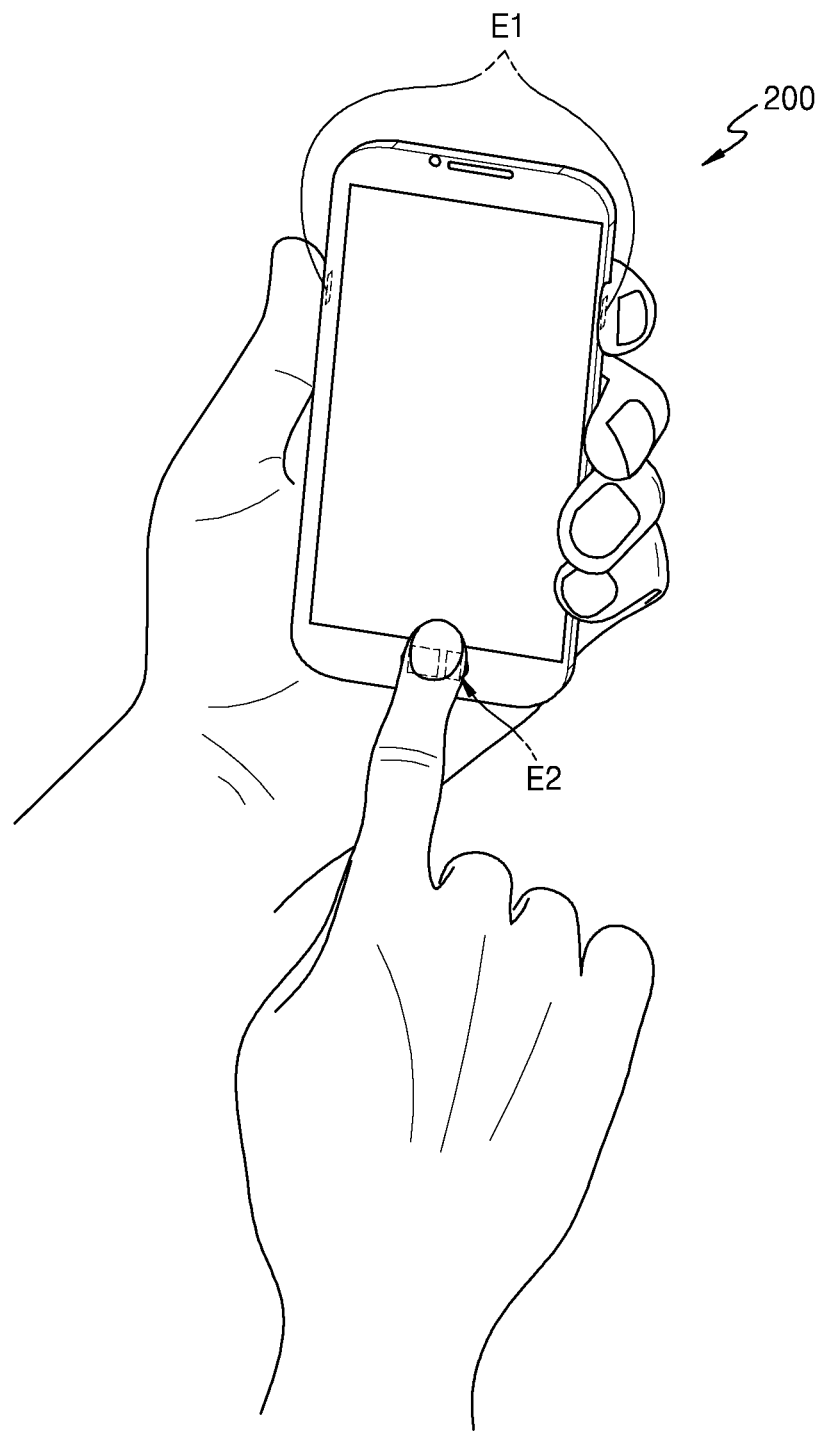
FIG. 9 illustrate an exterior of an apparatus for obtaining bio information and a case where a body part of a subject comes into contact with an electrode portion, according to another exemplary embodiment.

FIG. 9 illustrate an exterior of an apparatus 200 for obtaining bio information and a case where a body part of a subject comes into contact with an electrode portion, according to another exemplary embodiment.

As shown in FIG. 9, the apparatus 200 may be of a portable-device type. The apparatus 200 for obtaining bio information may include a front surface on which a display unit is disposed, a rear surface opposite to the front surface, and side portions connecting the front surface and the rear surface. A first electrode portion E1 may be arranged on the side portions. A current electrode and a voltage electrode of the first electrode portion E1 may be arranged on side portions which face each other from among four side portions. When the subject holds the apparatus 200 for obtaining bio information with one hand, two fingers of the hand may come into contact with the current electrode and the voltage electrode of the first electrode portion E1. In the drawing, the current electrode and the voltage electrode of the first electrode portion E1 are respectively arranged on the side portions of the apparatus 200 for obtaining bio information which face each other, but may be arranged on the same side portion. A second electrode portion E2 may be arranged on the front surface. A finger of the other hand which does not hold the apparatus 200 for obtaining bio information may be in contact with the second electrode portion E2.

FIG. 9 illustrates that the first electrode portion E1 is arranged on the side portions and the second electrode portion E2 is arranged on the front surface, but this is merely an example. The first electrode portion E1 may be arranged on the front surface and the second electrode portion E2 may be arranged on the rear surface.

Alternatively, the first electrode portion E1 and the second electrode portion E2 may be arranged on the front surface and the rear surface. That is, any one of the first electrode portion E1 and the second electrode portion E2 may be arranged on the front surface, and the other of the first electrode portion E1 and the second electrode portion E2 may be arranged on the rear surface. In this case, a palm of the hand on which the apparatus 200 for obtaining bio information is placed may be in contact with the first electrode portion E1 (or the second electrode portion E2), and a finger of the other hand on which the apparatus 200 for obtaining bio information is not placed may be in contact with the second electrode portion E2 (or the first electrode portion E1).

Alternatively, the first electrode portion E1 and the second electrode portion E2 may be arranged on the side portions and the rear surface. That is, any one of the first electrode portion E1 and the second electrode portion E2 may be arranged on the side portions, and the other of the first electrode portion E1 and the second electrode portion E2 may be arranged on the rear surface.

In at least one of the first electrode portion E1 and the second electrode portion E2, an area of the current electrode may be greater than an area of the voltage electrode. Besides the shape in FIG. 9, any one of the shapes illustrated in FIGS. 7A to 7F or FIGS. 8A to 8C, a combination thereof, or a modification of the shapes may be applied.

Examples, in which contact resistance between electrodes and body parts are differently set to decrease measurement errors when a bio impedance that may be used to analyze bio information is measured, have been described. An example in which an area of a current electrode is greater than an area of a voltage electrode has been mainly described, but the inventive concept is not limited thereto. In addition, various methods by which contact resistance of the current electrode is smaller than contact resistance of the voltage electrode may be used.

The apparatus for obtaining bio information sets electrode shapes by taking contact resistance between electrodes and body parts when a bio impedance is measured into account, and thus measurement accuracy of the bio impedance is improved.

Therefore, analysis accuracy of bio information using the measured bio impedance is improved.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An apparatus for obtaining bio information, the apparatus being a portable device comprising a front surface on which a display unit is arranged, a rear surface opposite to the front surface, and two side portions connecting the front and rear surfaces, the apparatus comprising:
    a first electrode portion comprising a first current electrode and a first voltage electrode, the first current electrode and the first voltage electrode being disposed on the two side portions, respectively, and arranged to be touchable by two fingers of a hand of a subject when the subject holds the apparatus with the hand;
    a second electrode portion comprising a second current electrode and a second voltage electrode, the second current electrode and the second voltage electrode being disposed on the front surface of the apparatus, and arranged to be simultaneously touchable by a single finger of another hand of the subject; and
    a measuring circuit configured to measure a body fat of the subject by applying a current to the first and the second current electrodes and detecting a voltage at the first and the second voltage electrodes while the first current electrode and the first voltage electrode are in contact with the two fingers, respectively and the second current electrode and the second voltage electrode are in contact with the single finger,
    wherein the second voltage electrode on the front surface have a shape surrounding the second current electrode, and
    wherein the first current electrode has an area greater than an area of the first voltage electrode, and the second current electrode has an area greater than an area of the second voltage electrode.

2. The apparatus of claim 1, wherein the second current electrode have a circular shape, and the second voltage electrode have a circular ring shape surrounding the second current electrode.

3. The apparatus of claim 2, wherein the second current electrode and the second voltage electrode satisfy a following condition:

$$a > \frac{-d + \sqrt{2b^2 - d^2}}{2}$$

where, a is a radius of the second current electrode, b is an external radius of the second voltage electrode, and d is a distance between the first current electrode and the first voltage electrode.

4. The apparatus of claim 1, wherein the second current electrode have a square shape, and the second voltage electrode have a square ring shape surrounding the second current electrode.

5. The apparatus of claim 4, wherein the second current electrode and the second voltage electrode satisfy a following condition:

$$a > \frac{-d + \sqrt{2b^2 - d^2}}{2}$$

where, a is a length of a side of the second current electrode, b is a length of an external side of the second voltage electrode, and d is a distance between the second current electrode and the second voltage electrode.

6. The apparatus of claim 1, wherein the second current electrode have an oval shape and the second voltage electrode have a oval ring shape surrounding the second current electrode.

7. The apparatus of claim 6, wherein the second current electrode and the second voltage electrode satisfy a following condition:

$$a > \frac{-(k+1)d + \sqrt{(k+1)^2 d^2 - 8k(d^2 - kb^2)}}{4k}$$

where, a is a length of a short axis of the second current electrode, b is a length of a short axis of an external oval of the second voltage electrode, d is a distance between the current electrode and the voltage electrode and k is a ratio of a long axis of the second current electrode to a short axis of the current electrode.

8. The apparatus of claim 1, further comprising an analysis unit configured to analyze the bio information of the subject based on a body impedance measured by the measuring circuit.

9. The apparatus of claim 3, wherein the bio information comprises body composition or blood volume.

* * * * *